(12) United States Patent
McEvoy

(10) Patent No.: US 7,268,669 B2
(45) Date of Patent: Sep. 11, 2007

(54) PERSONAL SENSORY REDUCTION SYSTEM, AND METHOD

(76) Inventor: Michael McEvoy, PMB 7917/P.O. Box 2428, Pensacola, FL (US) 32513

(*) Notice: Subject to any disclaimer, the term of this patent is extended or adjusted under 35 U.S.C. 154(b) by 0 days.

(21) Appl. No.: 10/982,745

(22) Filed: Nov. 5, 2004

(65) Prior Publication Data

US 2006/0097880 A1 May 11, 2006

(51) Int. Cl.
*G08B 1/00* (2006.01)

(52) U.S. Cl. .................. 340/309.16; 368/244; 381/372

(58) Field of Classification Search .......... 340/309.16, 340/573.1, 693.5, 693.9; 368/244, 10; 381/23.1, 381/312, 74, 370–372, 376, 378
See application file for complete search history.

(56) References Cited

U.S. PATENT DOCUMENTS

| | | | |
|---|---|---|---|
| 3,160,717 A | 12/1964 | Begula | |
| 3,271,520 A | 9/1966 | Fletcher | |
| 3,661,225 A | 5/1972 | Anderson | |
| 4,172,406 A * | 10/1979 | Martinez | .................. 84/464 R |
| 4,437,538 A | 3/1984 | Ohlsson | |
| 5,123,116 A * | 6/1992 | Roth | ................................ 2/15 |
| 5,241,971 A | 9/1993 | Lundin | |
| 5,333,622 A | 8/1994 | Casall | |
| 5,551,090 A | 9/1996 | Thompson | |
| 5,979,451 A | 11/1999 | Leight | |
| 5,996,123 A | 12/1999 | Leight | |
| 6,014,345 A | 1/2000 | Schmadeka | |
| 6,148,446 A | 11/2000 | Leight | |
| 6,164,409 A | 12/2000 | Berger | |
| 6,241,042 B1 | 6/2001 | Falco | |
| 2005/0046549 A1 * | 3/2005 | Hoyle | .................. 340/309.16 |

OTHER PUBLICATIONS

Halfbakery.com, Earplug Alarm Clock, posted to www.halfbakery.com on Aug. 4, 2004, 2 pages attached.
Hififorless.com, Online Catalog, posted Sep. 1, 2004, 12 pages attached.

* cited by examiner

*Primary Examiner*—Jeffery Hofsass
*Assistant Examiner*—Hongmin Fan
(74) *Attorney, Agent, or Firm*—David E. Herron, II

(57) ABSTRACT

The specification shows a personal sensory reduction system for limiting light and sound to a wearer's eyes and ears. A method for reducing the light and sound to eyes and ears is also shown and described.

18 Claims, 2 Drawing Sheets

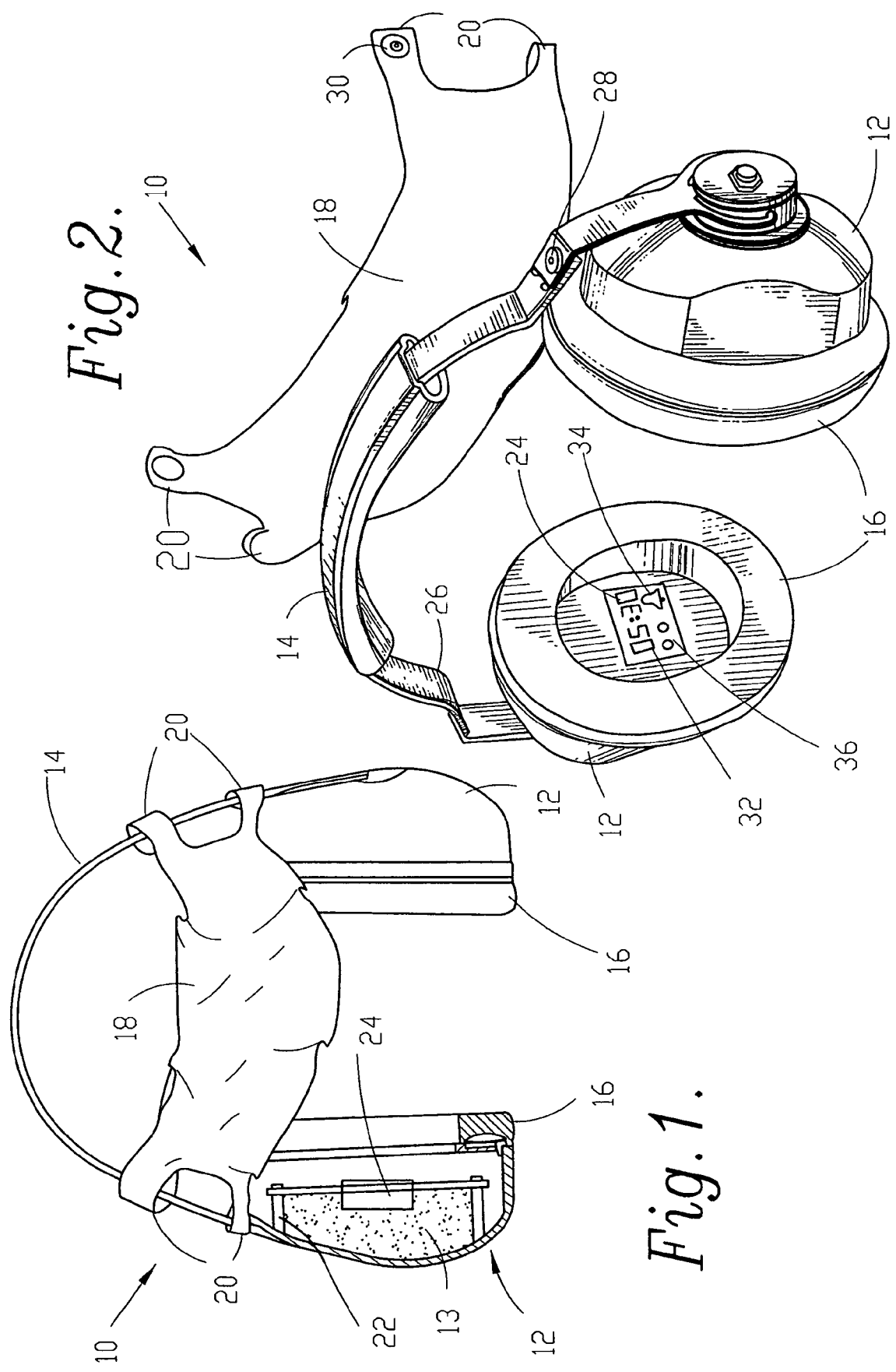

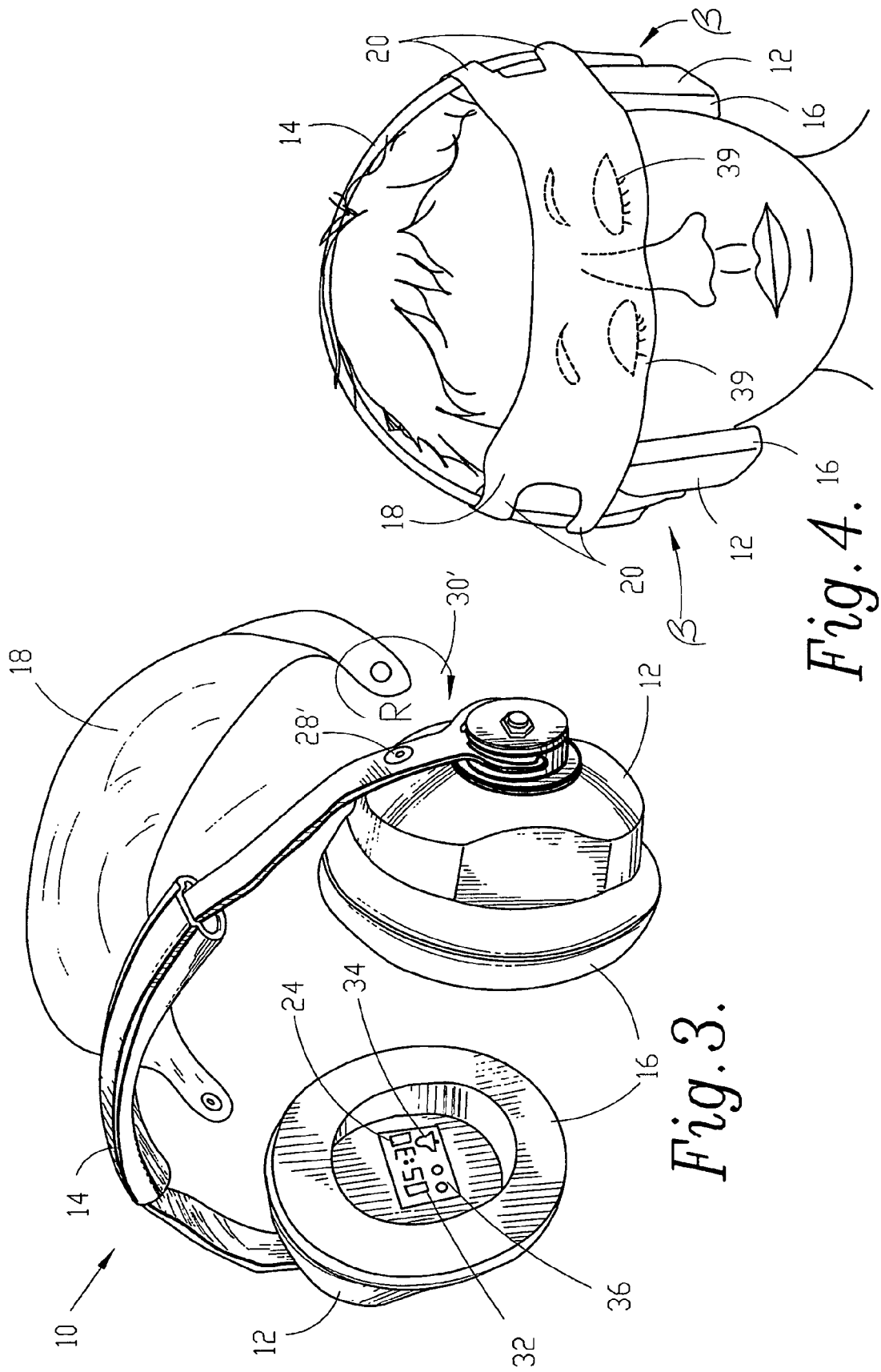

PERSONAL SENSORY REDUCTION SYSTEM, AND METHOD

SUMMARY OF THE INVENTION

The invention is a personal sensory reduction system for limiting light and sound to a wearer's eyes and ears; further, the invention is also a method for accomplishing the same.

THE INVENTIVE SYSTEM

The inventive system includes a headband having opposing ends, a blindfold, and a pair of dome-shaped structures positioned adjacent the respective opposing ends of the headband. Each dome shaped structure is adapted to envelop the ears of the wearer. A noise-attenuating means (i.e., foam padding, styrofoam, or annular layers) is positioned within an interior of each dome shaped structure, and an alarm is positioned to emit an auditory signal into the interior portion of at least one of the dome-shaped structures.

Optionally, the personal sensory reduction system may also include a timer in communication with the alarm to selectively activate the auditory signal. In a preferred embodiment of the personal sensory reduction system, the blindfold is removably attachable to the headband. Alternatively, the blindfold may be removably attachable to the dome-shaped structures.

Preferably, the blindfold will be a substantially opaque cloth that is removably attachable. The attachment may be accomplished by any known method of attachment, such as a button, a hook and loop fastener, a snap, a loop on the blindfold that surrounds the headband (also known as a rod pocket). Moreover, the blindfold may be a pivoting hood structure selectively positionable to shield the eyes of the wearer. In that event, the hood-structure should comprise a substantially opaque cloth attached to the headband. In preferred embodiments, the headband biases the dome-shaped structures over the ears of the wearer. The dome shaped structures may have padding that covers the edges.

THE INVENTIVE METHOD

The invention is also a method for limiting light and sound to a wearer's eyes and ears. The inventive method is accomplished by providing a headband having opposing ends, and placing a blindfold over the wearer's eyes, and positioning a pair of dome-shaped structures adjacent opposing ends of the headband. The inventive method further includes the steps of adapting the dome-shaped structures to envelop the ears of the wearer, and equipping an interior portion of each dome-shaped structure with a noise-attenuating means (for example, foam padding, styrofoam, a gelatin-filled chamber, annular layers, or the like), and placing an alarm inside at least one dome-shaped structure. The inventive method will also require one to configure the alarm to emit an auditory signal.

Optionally, the method may include the steps of providing a timer; and configuring the timer to selectively activate the auditory signal. In that regard, the method may also include the step of integrally forming the timer and the alarm inside the at least one dome-shaped structure.

In a preferred embodiment, the blindfold comprises a substantially opaque cloth that is removably attachable to either the headband or the dome-shaped structures. The attachment may be accomplished by any known means, such as a button, hook and loop fastener, snap, or a loop on the blindfold that allows the headband to pass. therethrough (commonly known as a rod-pocket).

In an alternate embodiment of the inventive method, the blindfold includes a pivoting hood structure selectively positionable to shield the eyes of the wearer. In this embodiment, the hood structure comprises a substantially opaque cloth attached to the system at either the dome-shaped structures or the headband.

The headband should bias the dome-shaped structures over the ears of the wearer. Further, the method may also include the step of padding the edges of each dome shaped structure.

Other objects, advantages and novel features of the present invention will become apparent from the following detailed description of the invention when considered in conjunction with the accompanying drawings.

BRIEF DESCRIPTION OF THE DRAWINGS

FIG. 1 is a frontal view of the inventive system according to the principles of the invention.

FIG. 2 is a perspective, exploded view of a first preferred embodiment, according to the principles of the invention.

FIG. 3 is a perspective, exploded view of a second preferred embodiment, according to the principles of the invention.

FIG. 4 shows the front view of invention, as it would be worn by a user.

DETAILED DESCRIPTION OF THE PREFERRED EMBODIMENTS

FIG. 1 shows a frontal view of the system 10. The system 10 includes a pair of dome-shaped structures 12 positioned adjacent opposing ends of a headband 14. The dome-shaped structures 12 are each equipped with padding 16 covering its edges. The padding 16 around the dome-shaped structures is configured to surround the ears of a wearer (not shown in FIG. 1; see FIG. 4) so that each dome-shaped structure 12 envelops a respective ear of its wearer.

Still referring to FIG. 1, the system 10 also includes a blindfold 18 that is configured to cover the eyes of a wearer (not shown in FIG. 1; see FIG. 4). The blindfold 18 is shown to be a substantially opaque cloth, but it could be a pliable plastic structure that may be rotatably attached to the system 10 so that it could shield the wearer's eyes.

Still referring to FIG. 1, a noise attenuating means 13 is positioned within the interior portion of the dome-shaped structures 12. The noise-attenuating means 13 may include foam padding, styrofoam, annular layers, gelatinous material, or the like.

A timer 24 is positioned inside at least one of the dome-shaped structures 12. In a preferred embodiment, the timer 24 is integrally formed within the interior portion of the dome-shaped structure 12. Alternately, the timer 24 may be held by a bracket 22 inside the dome-shaped structure 12.

In the embodiment shown in FIG. 1, the blindfold 18 is attached to the system 10 by a plurality of loops 20 that encircle the headband 14. Alternately, the blindfold 18 may be attached to the system 10 by any known means of attachment, such as buttons, snaps, hook-and-loop fasteners, or the like. Further, the blindfold may be affixed to the headband 14, the dome-shaped structures 12, or both.

FIG. 2 is a perspective view of the inventive system 10, which includes a headband 14 with dome-shaped structures 12 positioned adjacent respective ends of the headband 14. In this embodiment, a respective bend 26 is positioned near each end of the headband 14, and a connector 28 is affixed near the bend 26. The connector 28 on the headband is configured and positioned to meet a cooperating connector 30 that is positioned on the blindfold 18. The connectors 28, 30 may be any known type of connectors, such as buttons, snaps, or hook-and-loop fasteners. Of course, alternate designs for the blindfold 18 are also possible, and certainly fall within the spirit and scope of the invention. For example, the blindfold 18 may be a hood-like structure configured to cover the eyes of the wearer, such as a rotatable (yet pliable) opaque shield positionable over a wearer's eyes.

As shown in FIG. 2, the blindfold 18 may also be equipped with a loop 20 adjacent each opposing end 18 of the blindfold 18; the loop 20 may allow the headband to pass through, or it may be hooked onto the dome-shaped-structure 12.

Still referring to FIG. 2, foam padding 16 is positioned around the edges of the dome shaped structures 12. A timer 24 is inside at least one of the dome-shaped structures 12. This timer 24 may include a display 32 that may be selectively set by using buttons 36. The timer 24 should also be equipped with an alarm 34 that can emit an auditory signal at a time that is selectively input into the timer 24 by using the buttons 36. In order to suit personal preferences of a wearer, the auditory signal may be adjustable in volume.

FIG. 3 shows a perspective and exploded view of another embodiment of the inventive system 10. In this embodiment, the headband 14 lacks the bend (as in FIG. 2, for example), but instead is assumes a generally semi-circular shape configured to fit around a wearer's head. A connector 28' is positioned adjacent an end of the headband 14, and is configured to meet with a cooperating connector 30' positioned on the blindfold 18. Alternatively, the connector 28' may be positioned on the dome-shaped structure 12.

As shown in FIG. 3, the blindfold 18 may be a pliable yet opaque shield (i.e., made of plastic) that can be affixed to the system 10 and then rotatably positioned so that it can cover the eyes of a wearer. When a blindfold 18 is not desired, a wearer may either remove the blindfold 18 from the system 10 entirely, or pivotally rotate the blindfold 18 in direction R, out of one's line of sight. Also, the headband may include several telescoping segments, or segments that enable the headband and dome-shaped structures 12 to be folded onto one another, similar to "folding earmuffs" structure that has become known in the art.

Many of the remaining features of the embodiment shown in FIG. 3 are analogous to the features explained with respect to the embodiment in FIG. 2; as such a detailed discussion of these aspects is not necessary to understand the inventive system 10.

FIG. 4 shows a preferred embodiment of the system 10, as it would be worn by a user. The headband 14 creates a force B that biases the dome-shaped structures 12 over the ears of the wearer. In order to more effectively prevent light from contacting the wearer's eyes 39, the blindfold 18 should comprise an opaque material, such as felt, heavy cloth, or light-blocking or dark plastic. Loops 20 are positioned adjacent opposing ends of the blindfold 18, and may be attached to the system 10 either at the headband 14 (as shown) or by attaching to the dome-shaped structures 12.

Having described and illustrated the invention in detail, it is to be understood that the above and foregoing is for illustration and demonstration only. The description herein are not intended to limit the breadth of this invention.

I claim:

1. A personal sensory reduction system for limiting light and sound to a wearer's eyes and ears, the system comprising:
    a headband having opposing ends;
    a blindfold;
    a pair of dome-shaped structures, each dome shaped structure being positioned adjacent the respective opposing ends of the headband, and each structure including a head engaging surface configured to surround the wearer's ear, and an interior void that is adapted to envelop the ears of the wearer so that the dome shaped structure makes no contact with the ears of the wearer;
    a noise-attenuating means positioned within each dome shaped structure;
    an alarm positioned to emit an auditory signal into an interior portion of at least one of the dome-shaped structures
    a timer positioned within the at least one dome-shaped structure, and configured to be in communication with the alarm to selectively activate the auditory signal.

2. The personal sensory reduction system as in claim 1, wherein the blindfold is removably attachable to the headband.

3. The personal sensory reduction system as in claim 1, wherein the blindfold is removably attachable to the dome-shaped structures.

4. The personal sensory reduction system as in claim 1, wherein the blindfold comprises a substantially opaque cloth that is removably attachable to one of the headband or the dome-shaped structures by at least one of:
    a button;
    a hook and loop fastener;
    a snap;
    a loop on the blindfold that surrounds the headband.

5. The personal, sensory reduction system as in claim 1, wherein the blindfold includes a pivoting hood structure selectively positionable to shield the eyes of the wearer.

6. The personal sensory reduction system as in claim 5, wherein the hood-structure comprises a substantially opaque cloth attached to the headband.

7. The personal sensory reduction system as in claim 1, wherein the headband biases the dome-shaped structures over the ears of the wearer.

8. The personal sensory reduction system as in claim 1, further comprising padding covering edges of each dome shaped structure.

9. The personal sensory reduction system as in claim 1, wherein the noise attenuating means comprises at least one of:
    foam padding; or,
    styrofoam; or,
    annular layers.

10. A method for limiting light and sound to a wearer's eyes and ears, the method comprising the steps of:
    providing a headband having opposing ends;
    placing a blindfold over the wearer's eyes
    positioning pair of dome-shaped structures adjacent opposing ends of the headband;
    adapting the dome-shaped structures to envelop the ears of the wearer;
    equipping an interior portion of each dome-shaped structure with a noise-attenuating means;
    providing each dome shaped structure with a head engaging surface configured to surround the wearer's ear, and an interior void that is adapted to envelop the ears of the wearer so that the dome shaped structure makes no contact with the ears of the wearer;

placing an alarm and a timer inside at least one dome-shaped structure, and configuring the alarm and timer to selectively emit an auditory signal.

11. The method as in claim 10, further comprising the step of integrally forming the timer and the alarm inside the at least one dome-shaped structure.

12. The method as in claim 10, wherein the blindfold comprises a substantially opaque cloth that is removably attachable to the headband by at least one of:

a button;
a hook and loop fastener;
a snap;
a loop on the blindfold that allows the headband to pass therethrough.

13. The method as in claim 10 wherein the blindfold includes a pivoting hood structure selectively positionable to shield the eyes of the wearer.

14. The method as in claim 13, wherein the hood-structure comprises a substantially opaque cloth attached to the headband.

15. The method as in claim 10, wherein the headband biases the dome-shaped structures over the ears of the wearer.

16. The method as in claim 10, further including the step of padding edges of each dome shaped structure.

17. The method as in claim 10, wherein the noise attenuating means comprises at least one of:

foam padding; or,
styrofoam; or,
a gelatin-filled chamber; or
annular layers.

18. A personal sensory reduction system for limiting light and sound to a wearer's eyes and ears, the system comprising:

a headband having opposing ends and having a biasing means that urges each respective opposing end to remain adjacent one of the wearer's respective ears;

a blindfold removably attachable to the headband;

a pair of dome-shaped structures, each dome shaped structure being
positioned adjacent the respective opposing ends of the headband, and
adapted to envelop the ears of the wearer;

padding positioned around edges of each dome shaped structure;

noise reducing material positioned within an interior of each dome shaped structure;

an alarm positioned to emit an auditory signal into the interior portion of at least one of the dome-shaped structures a timer positioned within the interior portion and in communication with the alarm to selectively activate the auditory signal;

wherein the blindfold comprises a substantially opaque cloth that is removably attachable to the headband by at least one of:

a button;

a hook and loop fastener;

a snap;

a rod pocket on the blindfold configured to allow at least a portion of the headband to pass through the rod pocket.

* * * * *